(12) United States Patent
Robinson et al.

(10) Patent No.: US 7,631,448 B2
(45) Date of Patent: Dec. 15, 2009

(54) INDICATOR FOR IDENTIFYING LOCATION OF PROCEDURE

(75) Inventors: Philip Robinson, Bloomfield Hills, MI (US); Chester Czaplicka, Northville, MI (US); Marc Sakwa, Bloomfield Hills, MI (US)

(73) Assignee: RF Medical, Inc., Livonia, MI (US)

( * ) Notice: Subject to any disclaimer, the term of this patent is extended or adjusted under 35 U.S.C. 154(b) by 390 days.

(21) Appl. No.: 11/269,326

(22) Filed: Nov. 8, 2005

(65) Prior Publication Data

US 2007/0101628 A1    May 10, 2007

(51) Int. Cl.
*G09F 3/04* (2006.01)
*G09F 3/10* (2006.01)
*G09F 3/18* (2006.01)
*A61B 19/00* (2006.01)

(52) U.S. Cl. .................. 40/630; 40/638; 40/661.09; 40/299.01; 128/898

(58) Field of Classification Search .................. 40/630, 40/638, 661.09, 299.01; 128/898
See application file for complete search history.

(56) References Cited

U.S. PATENT DOCUMENTS

| | | | | | |
|---|---|---|---|---|---|
| 3,937,493 | A | * | 2/1976 | Fasbender | 283/41 |
| 4,787,158 | A | * | 11/1988 | Vitol | 40/638 |
| 5,366,087 | A | * | 11/1994 | Bane | 206/459.5 |
| 5,879,453 | A | * | 3/1999 | Streeter et al. | 118/31.5 |
| 5,947,917 | A | * | 9/1999 | Carte et al. | 602/52 |
| 5,958,536 | A | * | 9/1999 | Gelsinger et al. | 428/40.1 |
| 5,979,941 | A | * | 11/1999 | Mosher et al. | 283/67 |
| 6,036,231 | A | * | 3/2000 | Foote et al. | 283/67 |
| 7,140,135 | B2 | * | 11/2006 | Irvine et al. | 40/638 |
| 2002/0014029 | A1 | * | 2/2002 | Copelan | 40/638 |

* cited by examiner

*Primary Examiner*—Lesley D Morris
*Assistant Examiner*—Syed A Islam
(74) *Attorney, Agent, or Firm*—Brinks Hofer Gilson & Lione

(57) ABSTRACT

The first and second portion may comprise a first and second sticker where the first and second sticker includes a dermal adhesive allowing the sticker to be securely fastened to the skin of the patient. Further, the first and second portion may include a symbol identifying the location of the procedure, the type of procedure or a serial number associating the first and second portion.

5 Claims, 6 Drawing Sheets

INDICATOR FOR IDENTIFYING LOCATION OF PROCEDURE

BACKGROUND

1. Field of the Invention

The present invention generally relates to an indicator for identifying the location of a surgical procedure on a patient.

2. Description of Related Art

Prior to performing a medical surgical procedure on a patient, the patient is prepared for the procedure. Often a nurse will review the medical records of the patient and identify the procedure to be performed. Generally a few hours before the procedure, a nurse will draw an "X" on the patient where the procedure is to be performed. The "X" or mark is drawn on the skin of the patient with an indelible ink. Since it is drawn by hand, the marks are not consistent between patients or procedures due to the changes in hospital staff. The patient is not involved in marking the location and often the surgeon is not present. Further, the location of the mark and any verification signatures are generally not entered into the patient's records. Lack of structure in this procedure and misinterpretation of the handwritten markings may lead to a misidentification of the procedure location. Further, additional verification would increase the viability and consistency of the identification and reduce the risk of misinterpretation.

In view of the above, it is apparent that there exists a need for an improved method and device for identifying a procedure location on a patient.

SUMMARY

In satisfying the above need, as well as overcoming the enumerated drawbacks and other limitations of the related art, the present invention provides an indicator which is applied to the patient for identifying the location of the procedure on a patient. The indicator includes a first portion being indicative of a first location approval, and a second portion being indicative of a second location approval. The first and second portions are configured to attach to the patient and cooperate to provide a visual confirmation of the first and second location approvals. The visual confirmation may be due to an interacting geometry between the first and second portion, or the visual confirmation may be color coded such that the visual confirmation is cooperatively formed by a first color on the first portion and a second color on the second portion.

The first and second portions may comprise a first and a second sticker, where the first and second stickers include a dermal adhesive allowing the sticker to be securely fastened to the skin of the patient. Further, the first and second portions may include a symbol identifying the location of the procedure, the type of procedure or a serial number associating the first and second portions.

Further, the indicator may be included on a form, where the form has a verification region corresponding to the first portion of the indicator. The first verification region is provided for a patient's signature. Similarly, the second portion of the indicator corresponds to a second verification region provided for the signature of hospital staff. In addition, the form may include a procedure block for identification of the procedure and a surgeon block for identification of the surgeon. The form may also include an adhesive allowing the signed form to be mounted directly into the medical records of the patient. Holes may also be provided and appropriately spaced allowing the form to be pinned into the file of the patient.

Further objects, features and advantages of this invention will become readily apparent to persons skilled in the art after a review of the following description, with reference to the drawings and claims that are appended to and form a part of this specification.

DETAILED DESCRIPTION

Figure 1:
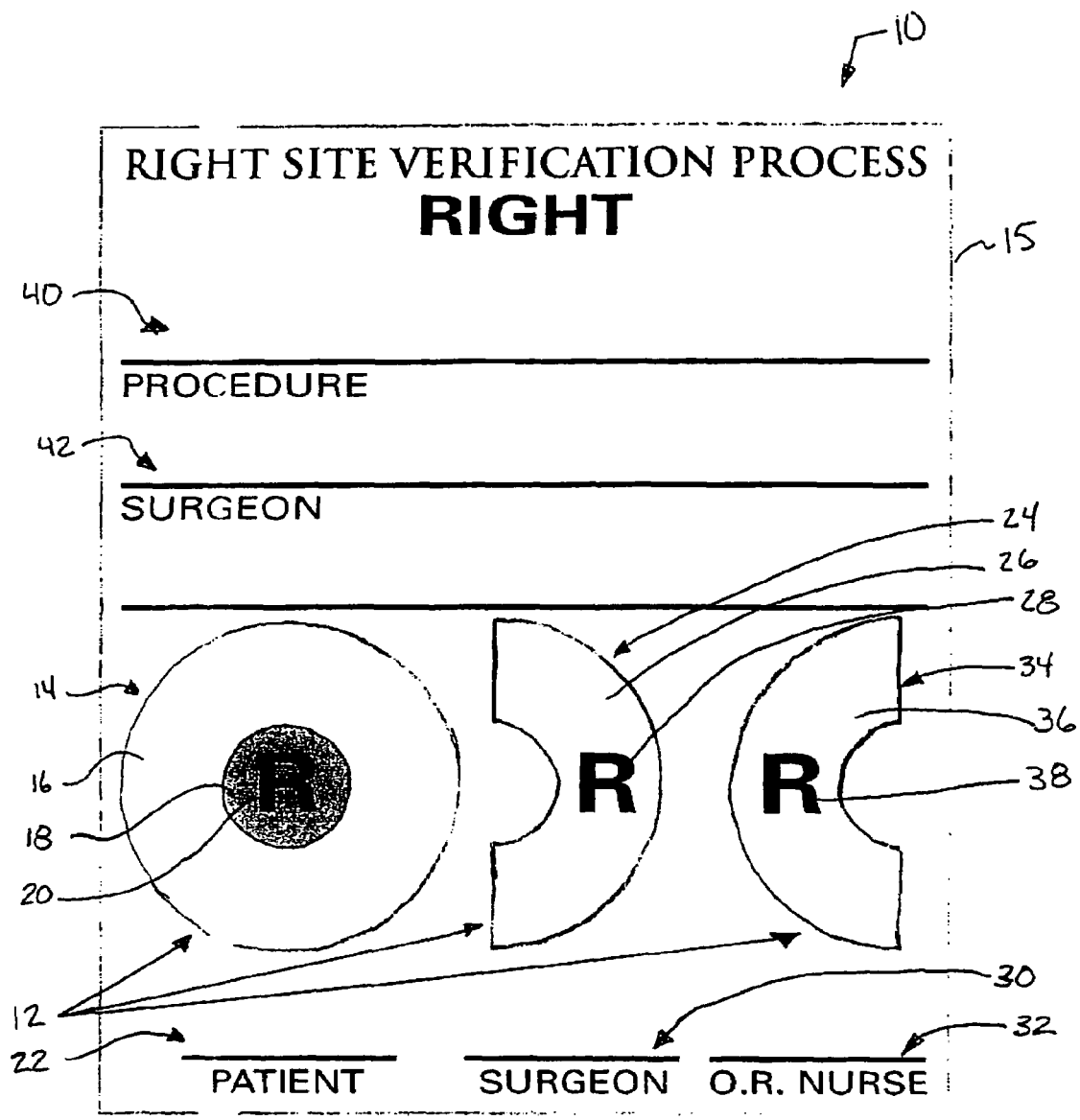
FIG. 1 is a plan view of a form including an indicator in accordance with the present invention.

Referring now to FIG. 1, a system embodying the principles of the present invention is illustrated therein and designated at 10. The system 10 includes an indicator 12 for verifying the location of the procedure on a patient. The indicator 12, as shown, includes a first portion 14, a second portion 24, and a third portion 34. The first, second and third portions 14, 24, 34 are included as part of a form 15. The first portion 14 is shown as a sticker having a generally circular geometry. The first portion 14 has an annular region 16 formed about a circular region 18 and located concentrically therewith. In addition, the first portion 14 has a symbol 20 printed on the circular region 18 and configured to be legible prior to the procedure. The symbol 20 may be indicative of a location of the procedure, a type of procedure, a serial number, or any combination thereof. For example, the symbol 20 may include an "R" indicative of the right side of the patient, thereby verifying the location of the procedure. However, the symbol 20 may include any combination of letters, numbers or graphics for any of the purposes previously described herein.

A verification block 22 may be located on the form 15 and aligned with the first portion 14. The verification block 22 may be identified as a patient signature block such that the patient may sign the verification block 22 as he removes the first portion 14 of the indicator 12 from the form 15 and attaches the first portion 14 to the procedure location. The verification block 22 may include other common forms of verification, such as fingerprints or social security numbers.

The second portion 24 of the indicator 12 is also shown as a sticker. The second portion 24 includes a semi-annular region 26 corresponding to a portion, such as half, of the annular region 16. The second portion 24 also includes a symbol 28 that may be indicative of the location of the procedure, the type of procedure, or a serial number relating to the first portion 14. Preferably, the symbol 28 would be identical to, or cooperate with, the symbol 20 on the first portion 14 of the indicator to create predetermined indicia, also providing a visual confirmation of the procedure location. The second portion 24 is aligned with a verification block 30. The verification block 30 may be a signature block for the surgeon and may be labeled as such. However, as previously mentioned herein, other common forms of verification may be used.

A third portion 34 of the indicator 12 is also attached to the form 15. The third portion 34 includes a semi-annular region 36 that corresponds to the annular region 16 of the first portion 14. In addition, the semi-annular region 36 may compliment the semi-annular region 26 of the second portion 24, such that the semi-annular region 26 and semi-annular region 36 cooperate to form a shape corresponding to the annular region 16 of the first portion 14. The third portion 34 may also include a symbol 38. As previously described, the symbol 38 may be indicative of a location, a procedure, a serial number, or any combination thereof. The third portion 34 is aligned with a verification block 32. The verification block 32 may be a signature block for hospital staff, such as a nurse, and may be identified as such. Although, other commonly used identifiers may be used in verification block 32, as described previously herein, with relation to verification blocks 22 and 30. The form 15 may also include a procedure block 40 for indicating the procedure to be performed on the patient. In addition, a surgeon block 42 may also be provided to indicate the surgeon that will perform the procedure identified by the procedure block 40.

As described above, the first, second and third portion 14, 24, 34 are shown as stickers and therefore may include a dermal adhesive on a backside of the first, second and third portion 14, 24, 34. Accordingly, the form 15 may be made of a non-stick paper, such that the indicator 12 may be peeled off of the form 15. However, the form 15 may also be configured such that the indicator 12 is die cut into the form 15. As such, the form 15 is attached to a non-stick backing. After the indicator 12 is removed from the form 15, the rest of the non-stick backing may be removed such that form 15 may be mounted into the medical records of the patient using the adhesive attached to the form 15.

Figure 2:
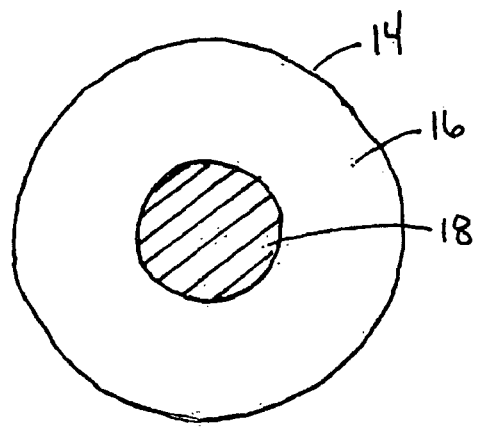
FIG. 2 is a plan view of the first portion of the indicator removed from the form and attached to the patient.
Figure 3:
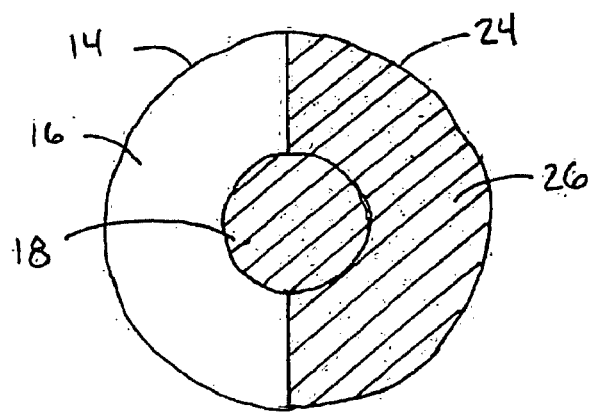
FIG. 3 is a plan view of the first and second portion of the indicator forming a visual confirmation in accordance with the present invention.

Now referring to FIG. 2, the first portion 14 is shown after attachment to the patient. The annular region 16 may include a first color, such as yellow. The circular region 18 may include a second color, such as green. The second portion 24 may be attached to the patient and located within the annular region 16 of the first portion 14, as shown in FIG. 3. Further, the semi-annular region 26 of the second portion 24 may be made of a transparent blue material such that the first color of the annular region 16, such as yellow, may cooperate with the color of the second portion 24, such as a transparent blue, to form a green that matches the second color of the circular region 18. As such, the first and second portions cooperatively form a color coded visual confirmation. Alternatively, the second portion 24 may be made of an opaque material including a color that matches the second color of the circular region 18. Accordingly, as the second portion 24 is mounted on and covers a portion of the annular region 16, a continuous colored geometry is cooperatively formed by the second portion 24 and the circular region 18, thereby providing a visual confirmation of the procedure location.

Figure 4:
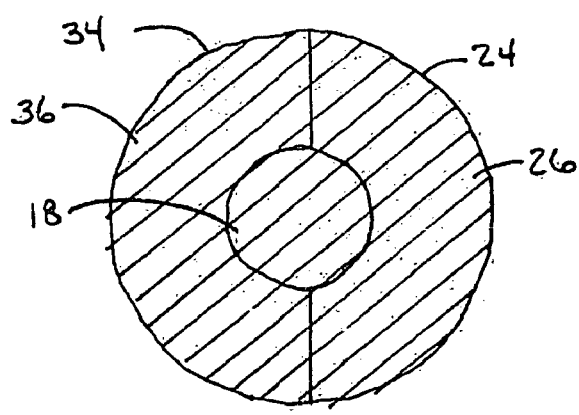
FIG. 4 is a plan view of the first, second and third portion of the indicator cooperatively forming a visual confirmation of the procedure location in accordance with the present invention.

Now referring to FIG. 4, a third portion 34 may be mounted on the annular region 16 in a complimentary manner to the semi-annual region 26 of the second portion 24 to fully cover the annular region 16. Similarly to the second portion 24, the third portion 34 may also form a color coded or geometric visual confirmation that cooperates with the first and second portion 14, 24. Accordingly, the third portion 34 may be made of a transparent material of a color, such as blue, that when mounted on the annular region 16 of a color, such as yellow, would thereby produce a green color matching the color of the circular region 18 of the first portion 14. Alternatively, the third portion 34 may be made of an opaque material having a color that matches the second color of the circular region 18. As such, the first, second and third portions 14, 24, 34 may all cooperate to form a contiguous region of a common color and may also cooperate to form a common geometry such as a circle thereby providing a three part visual confirmation of the procedure location. Each of the first, second, and third portions 14, 24, 34 correspond to and are indicative of a location approval. The location approval may include the act of each individual placing the sticker at the procedure site, or more definitively, the location approval may include the location approval of the patient via patient signature in verification block 26, the location approval of the surgeon via a surgeon signature in verification block 36, and the location approval of a nurse via a nurse signature in verification block 32.

In addition, it would be readily apparent to one of ordinary skill in the art, that from the embodiment described a two-part verification could be provided such that two stickers or marks could be combined to form a continuous color coded region or to form a common geometric shape thereby providing a visual confirmation in accordance with the present invention.

Figure 5:
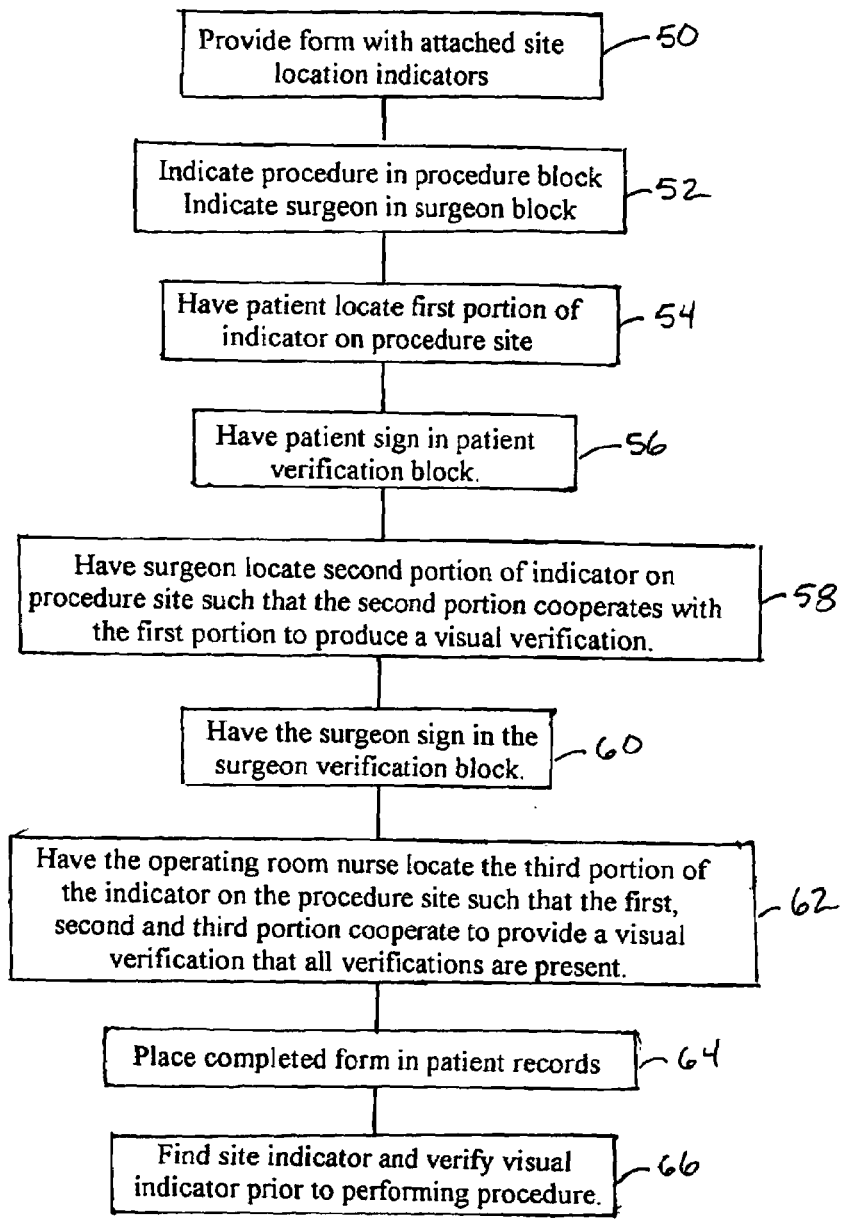
FIG. 5 is a flow chart of a method for verifying the location of a procedure on a patient in accordance with the present invention.

Now referring to FIG. 5, a method to provide a visual confirmation of a procedure location in accordance with the present invention is illustrated. In block 50, a form 50 is provided with a site location indicator 12 attached thereto. A hospital staff member such as a surgeon or nurse indicate the procedure to be performed in a procedure block 40 and the surgeon to perform the procedure in the surgeon block 42 of the form 15, as indicated by block 52. In block 54, the patient attaches the first portion 14 of the indicator 12 on the procedure site. As previously discussed, this may be by peeling a sticker from the form 15 and placing it on the site, or alternatively by providing a stamp or other marking on or near the procedure site. The patient may then sign in the patient verification block as denoted by block 56. A surgeon may then locate the second portion 24 of the indicator on the procedure site such that the second portion 24 of the indicator 12 cooperates with the first portion 14 of the indicator 12 to produce a visual confirmation of the procedure location, as denoted by block 58. In block 60, the surgeon may sign the surgeon verification block on the form 15. In block 62, another hospital staff member, such as an operating room nurse, locates the third portion 34 of the indicator 12 on the procedure site, such that the first, second, and third portion 14, 24, 34 of the indicator 12 cooperate to provide a visual confirmation that all three verifications are present. As previously described, the visual confirmation may take the form of matching symbols, cooperating geometries, coordinating colors, or any combination thereof.

In block 64, the completed form may be placed in a patient's record either by using holes located in the form to pin the form in the patient records, or by mounting the form in the patient records using adhesive attached to the form. In block 66, the indicator 13 is found at the site and the visual confirmation is checked prior to performing the procedure, as denoted in block 66.

Figure 6:
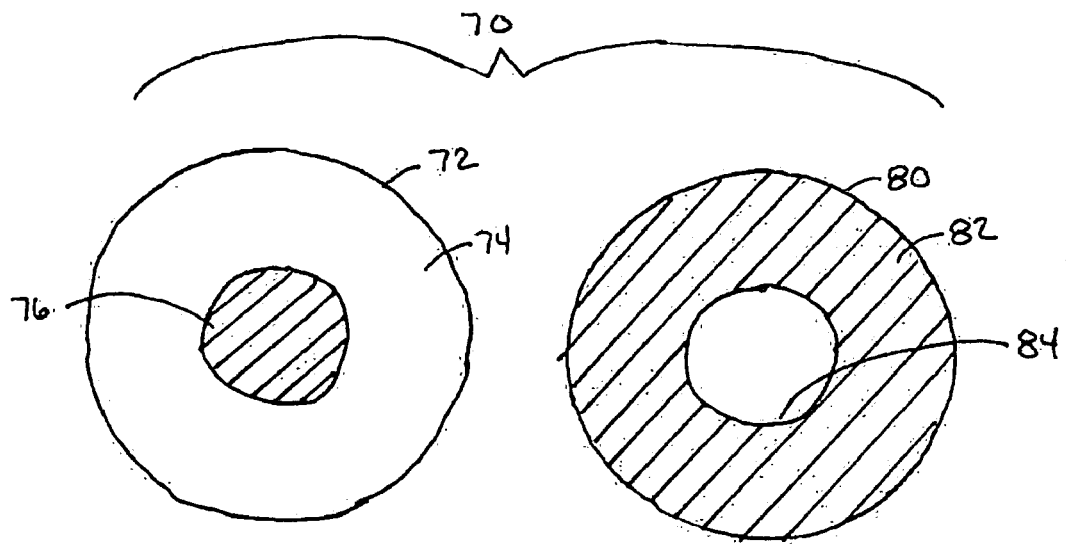
FIG. 6 is a plan view of an embodiment of a two-part indicator in accordance with the present invention.
Figure 7:
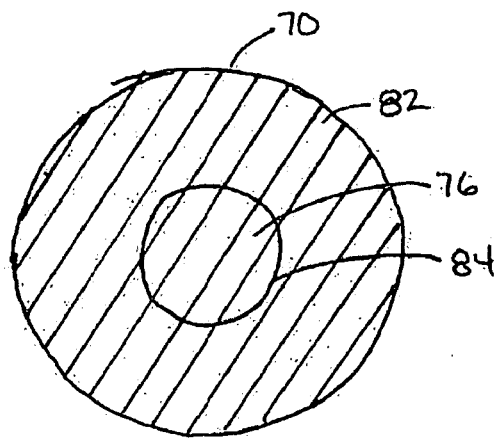
FIG. 7 is a plan view of the two-part indicator forming a visual confirmation in accordance with the present invention.

Now referring to FIG. 6, a two-part indicator 70 is illustrated. The first portion 72 of the two-part indicator 70 is similar to the first portion 14 of the indicator 12 described above. The first portion 72 has an annular region 74 including a first color or pattern and a second circular region 76 including a different color or pattern. The second portion 80 has an annular region 82 corresponding to the annular region 74 of the first portion 72. In addition, the second portion 80 has a circular hole 84 corresponding to the circular region 76 of the first portion 72. As such, the first portion 72 may be placed at the procedure location on the patient and the second portion 80 is attached to the annular region 74 of the first portion 72 such that the circular region 76 fills the hole 84 of the second portion 80, as shown in FIG. 7. Accordingly, the first portion 72 and the second portion 80 cooperate to form a contiguous circular region of a matching pattern or color thereby providing a visual confirmation to the hospital staff of the procedure site location.

Figure 8:
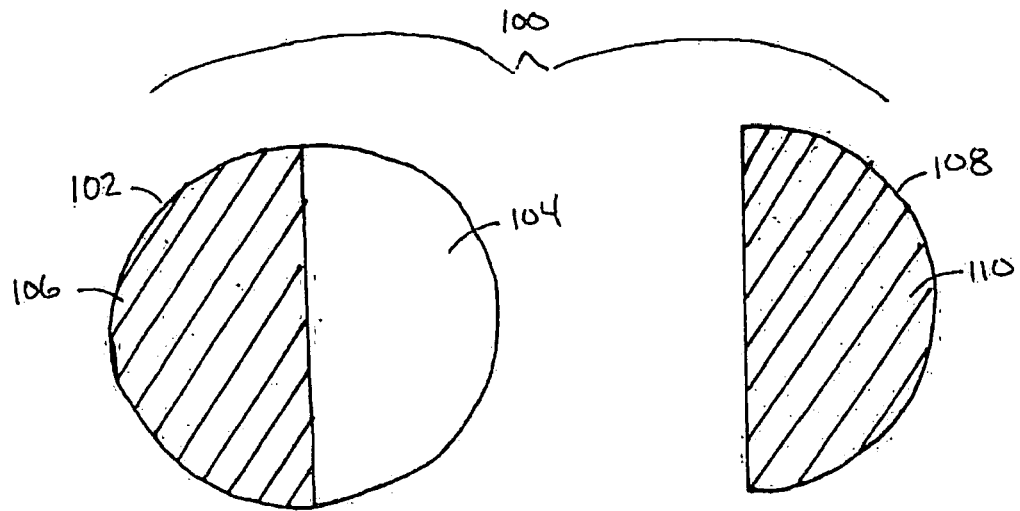
FIG. 8 is a plan view of another embodiment of a two-part indicator wherein the first and second portion have the same geometric shape in accordance with the present invention.
Figure 9:
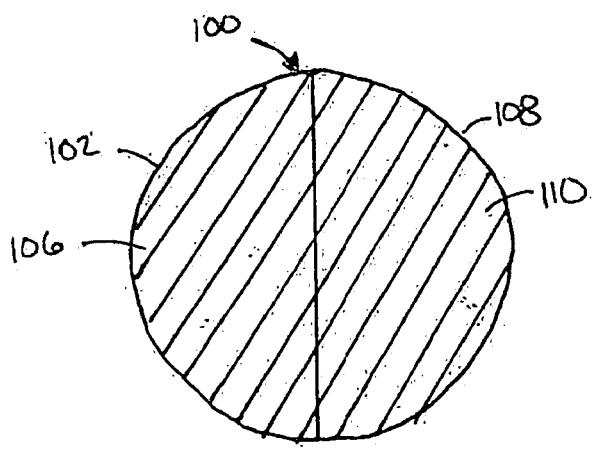
FIG. 9 is a plan view of the indicator of FIG. 8 cooperatively forming a visual confirmation in accordance with the present invention.

Now referring to FIG. 8, another two-part indicator 100 is provided. A first portion 102 of the two-part indicator 100 includes a semi-circular region 106 having a first pattern or color and optionally may include a second semi-circular region 104 including a second color or pattern different from the first semi-circular region 106. The second portion 108 also includes a semi-circular region 110 that is complimentary to the semi-circular region 106 of the first portion 102. Accordingly, the first portion 102 may be attached to the patient at the procedure site location and the second portion 108 may be placed adjacent to the first portion 102, such that the semi-circular region 108 and the semi-circular region 110 cooperate to form a circular geometry having a consistent color or pattern. The second portion 108 may be placed on the semi-circular region 104 or alternatively, the first portion may omit the semi-circular region 104 and the second portion 108 may be directly attached to the patient's skin adjacent to the first portion 102 also forming a circular geometry to provide a visual confirmation of the procedure location.

Figure 10:
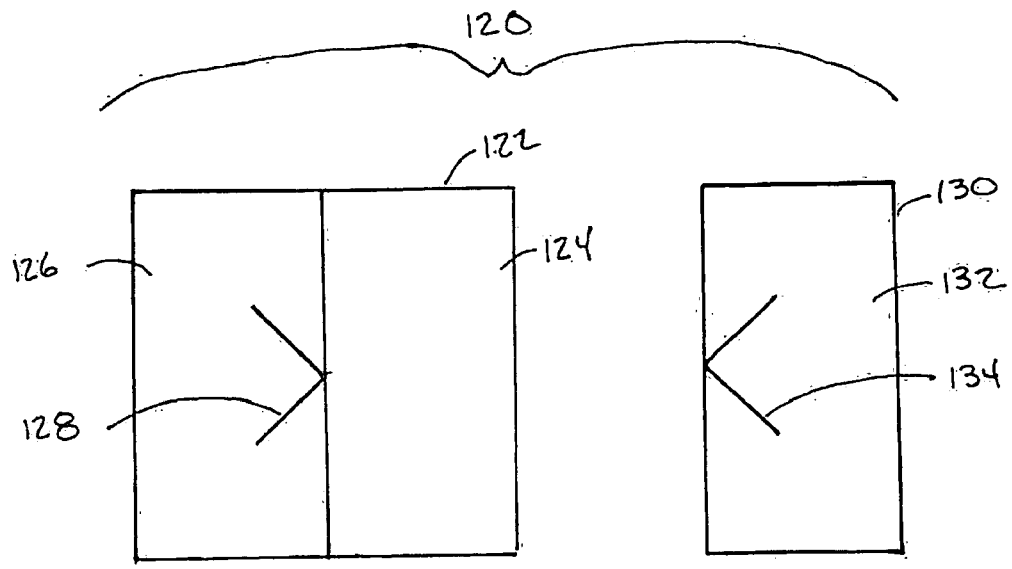
FIG. 10 is a plan view of another embodiment of an indicator having a square shape and including a symbol on each portion.
Figure 11:
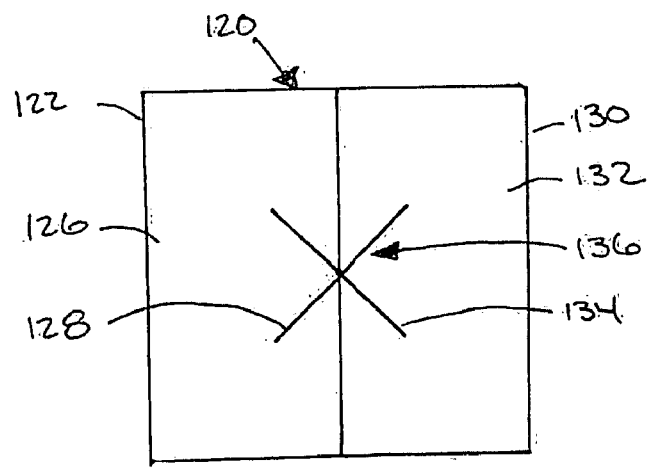
FIG. 11 is a plan view of the indicator of FIG. 10 where the symbol on the first and second portion cooperate to form a visual confirmation in accordance with the present invention.

Now referring to FIG. 10, another indicator using a symbol as a visual confirmation is provided. The indicator 120 includes a first portion 122 and a second portion 130. The first portion 122 includes a rectangular region 126 including a symbol 128 shown as an arrow or a half "X". In addition, a second region 124 may optionally be provided. The second portion 130 includes a rectangular region 132 including a symbol 134 shown as a backward arrow or a second half of an "X". The first portion 122 may be attached by the patient at the procedure site location. The rectangular region 132 of the second portion 130 may be located adjacent the rectangular region 126 of the first portion 122 and attached to the patient or optionally the rectangular region 124. As such, the first symbol 128 may be aligned with the second symbol 134 forming a graphic or symbol, shown as an "X" and denoted as reference numeral 136. Accordingly, the first symbol 128 and the second symbol 134 cooperate to form a visual confirmation 136 of the procedure site location, as shown in FIG. 11. In addition, the rectangular region 124 and the rectangular region 132 cooperate to form a square geometry, thereby providing a geometric visual confirmation as well.

Clearly, one of ordinary skill in the art can envision other modifications in the form of visual confirmation including other symbols, geometries, and colors that are contemplated within the significant advancement of the art that falls within the scope of the present invention.

Further, as a person skilled in the art will also readily appreciate, the above description is meant as an illustration of the principles this invention. This description is not intended to limit the scope or application of this invention in that the invention is susceptible to modification, variation and change, without departing from the spirit of this invention, as defined in the following claims.

We claim:

1. A method for identifying a procedure location on a patient, the method comprising:
    providing an indicator having a first and second portion, the first portion being indicative of a first location approval and the second portion being indicative of a second location approval;
    attaching the first portion of the indicator to the patient at the procedure location; and
    attaching the second portion of the indicator to the patient at the procedure location such that the first and second portion cooperate to provide a visual confirmation of the first and second location approval.

2. The method according to claim 1, further comprising verifying the first location approval in a verification block.

3. The method according to claim 1, wherein the first verification block is located on a form and comprising the step of attaching the form to a medical file of the patient.

4. The method according to claim 1, wherein the first and second portions are attached to the patient to cooperatively form a contiguous geometric shape to provide the visual confirmation.

5. The method according to claim 1, wherein the first and second portion cooperatively form indicia to provide the visual confirmation.

* * * * *